United States Patent
Tong et al.

(10) Patent No.: US 10,808,270 B2
(45) Date of Patent: Oct. 20, 2020

(54) METHOD FOR CONTINUOUSLY PRODUCING STARCH SACCHARIFICATION PRODUCTS BY USING HIGH-CONCENTRATION STARCH MILK

(71) Applicant: COFCO Limited, Beijing (CN)

(72) Inventors: Yi Tong, Beijing (CN); Anni Liu, Beijing (CN); Yi Li, Beijing (CN); Bo Chen, Beo (CN); Jin Tao, Beijing (CN)

(73) Assignee: COFCO Limited, Beijing (CN)

(*) Notice: Subject to any disclaimer, the term of this patent is extended or adjusted under 35 U.S.C. 154(b) by 0 days.

(21) Appl. No.: 16/750,509

(22) Filed: Jan. 23, 2020

(65) Prior Publication Data

US 2020/0248220 A1    Aug. 6, 2020

(30) Foreign Application Priority Data

Feb. 1, 2019    (CN) .......................... 2019 1 0105943

(51) Int. Cl.
| | | |
|---|---|---|
| *C12P 19/00* | (2006.01) | |
| *C12P 19/14* | (2006.01) | |
| *C12P 19/02* | (2006.01) | |

(52) U.S. Cl.
CPC ............... *C12P 19/14* (2013.01); *C12P 19/02* (2013.01); *C12Y 302/01003* (2013.01); *C12Y 302/01041* (2013.01); *C12Y 302/01001* (2013.01)

(58) Field of Classification Search
None
See application file for complete search history.

(56) References Cited

FOREIGN PATENT DOCUMENTS

| CN | 1358863 A | 7/2002 |
|---|---|---|
| CN | 101939442 A | 1/2011 |
| CN | 103981239 A | 8/2014 |
| CN | 104911234 A | 9/2015 |

*Primary Examiner* — Thane Underdahl
(74) *Attorney, Agent, or Firm* — Duane Morris LLP

(57) ABSTRACT

The present disclosure provides a method for continuously producing starch saccharification products by using high-concentration starch milk.

20 Claims, 1 Drawing Sheet

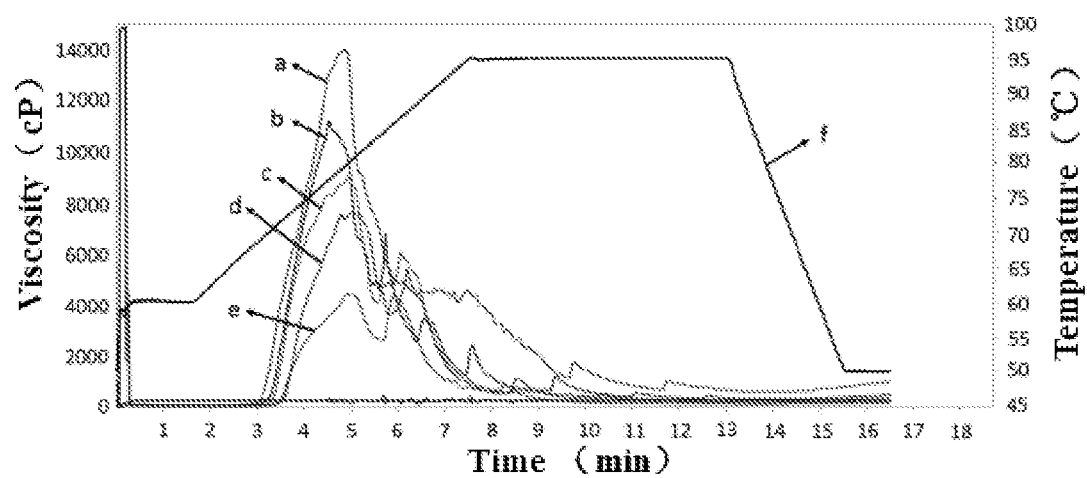

ary important to improve quality and reduce production cost of the starch sugar products. In recent years, the enzymatic hydrolysis sugar-making process has gradually replaced the acid method sugar-making process. Generally, the enzymatic hydrolysis sugar-making process is generally divided into the liquefaction and saccharification stages as follows: initially liquefying the starch milk with amylase having a high specificity to obtain a starch liquefaction product (liquefied liquid) containing dextrin and/or oligosaccharide, and subsequently using a saccharifying enzyme to further saccharifying the obtained starch liquefaction product into a starch saccharification product containing glucose (saccharified liquid), that is, the starch sugar. The enzymatic reaction has mild conditions, less side reactions and high conversion efficiency. However, the enzymatic reaction takes a longer time, and it is difficult to filter enzymes because the enzymes are proteins.

At present, the most commonly used starch liquefaction process in the liquefaction stage of the enzymatic hydrolysis sugar-making process is a spray liquefaction technology. The spray liquefaction technology generally comprises a pre-liquefaction treatment stage and a liquefaction treatment stage. In the pre-liquefaction treatment stage, starch is generally added with water and subjected to a size mixing to form starch milk, a protective agent and an activating agent of amylase are added after adjusting the pH, and finally a high-temperature resistant alpha-amylase is added. During the liquefaction treatment stage, the uniformly stirred starch milk is pumped into a spray liquefier, such that the sprayed starch milk is directly contacted with the high-temperature steam. In order to meet the requirements on activity of the high-temperature resistant alpha-amylase and the spray liquefaction, the temperature of steam is usually controlled to be within a range of 90-120° C., and the pressure is controlled to be within a range of 0.9-1.2 MPa. The spray liquefaction technology utilizes the high-temperature steam to rapidly heat the starch milk, and can limit the viscosity increase of the starch in a short time. However, the starch gelatinization phenomenon is still very severe at the above temperatures and the limitation of viscosity on the technological process is still very significant, thus it is generally difficult to increase the initial concentration of the starch milk to 35% or more. On the other hand, when an indirect heating is used, the starch is heated for too long, it results in the excessively high viscosity of the liquefied liquid, which makes the pumping and the subsequent processing to be very complicated.

In the enzymatic hydrolysis sugar-making process, the initial concentration of starch milk is increased, which causes technical problems in two aspects as follows: 1) during the liquefaction stage, the viscosity of high-concentration starch is sharply increased in the heating gelatinization process, so that the liquefaction control becomes difficult, it imposes adverse effects on the equipment operation and liquefied liquid quality; 2) during the saccharification stage, an increased concentration of the substrate may cause the glucose to carry out a composite reaction to generate a large amount of disaccharide and trisaccharide, thereby reducing the glucose yield. In order to avoid the aforementioned technical problems, the currently common practice of the industry is to control the initial concentration of starch milk to be within a lower range of 31-33%.

However, the saccharified liquid needs to be concentrated (for example, being concentrated to 45%) in the later stage of sugar solution evaporation process in the starch sugar production, the low initial concentration range of starch milk cannot overcome the problems of high energy consumption and large water consumption caused by sugar solution evaporation in the later stage of starch sugar production. Therefore, it is necessary to increase the initial concentration of starch moderately in the starch sugar production process so as to decrease energy consumption, increase productivity, reduce costs and improve efficiency.

Therefore, there is an urgent need for an improved process for producing the starch saccharification products which achieve the balance among energy consumption reduction, viscosity control and glucose yield in the production process of the starch saccharification products.

SUMMARY

In order to solve the above technical problems, the present disclosure provides an improved method for producing saccharified starch products, the method is capable of effectively controlling the viscosity of starch during heating and gelatinization process in a liquefaction stage while increasing the initial concentration of starch. In addition, the method can also effectively inhibit the occurrence of composite reaction in the saccharification stage and ensure the yield of glucose in the starch saccharification products, thereby achieving the balance among energy consumption reduction, viscosity control and glucose yield in the production process of the starch saccharification products. Specifically, the above object of the present disclosure is achieved by the following aspects:

In a first aspect, the present disclosure provides a method for producing starch saccharification products by using high-concentration starch milk, wherein the method comprises the following steps:

(1) a pre-liquefaction step: adding medium-temperature alpha-amylase, high-temperature resistant alpha-amylase, lipase and neutral protease into starch milk having a pH of 5.0-6.0 and a dry basis mass fraction of 38 wt %-55 wt %, mixing and preserving heat at a temperature of 45-60° C., preferably 55-60° C. for 0.5~1.5 hours to obtain a first starch milk;

(2) a liquefaction step: performing spray liquefaction on the first starch milk, carrying out heat preservation for 3-5 min and then implementing flash evaporation, lowering the temperature of a product after flash evaporation to 97-99° C., and subsequently carrying out heat preservation for 0.5-3 hours at a temperature of 95-97° C. to obtain a starch liquefaction product; and (3) a saccharification step: adjusting a pH of the starch liquefaction product to a range of 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

In a second aspect, the present disclosure provides a method for continuously producing starch saccharification products by using high-concentration starch milk, wherein the method comprises the following steps:

(1) a first pre-liquefaction step: adding medium-temperature alpha-amylase, high-temperature resistant alpha-amylase, lipase and neutral protease into starch milk having a pH of 5.0-6.0 and a dry basis mass fraction of 38 wt %-55 wt %, and preserving heat at a temperature of 45-60° C., preferably at 55-60° C. for 0.5-1.5 hours to obtain a first starch milk;

(2) a second pre-liquefaction step: adding starch into the first starch milk and stirring to obtain a second starch milk having a dry basis mass fraction of 50 wt %-70 wt %, adding medium-temperature alpha-amylase, high-temperature resistant alpha-amylase, lipase and neutral protease into the second starch milk, and preserving heat at a temperature of 50-60° C. for more than 0.5 hour to obtain a third starch milk;

(3) a liquefaction step: performing spray liquefaction on the third starch milk, carrying out heat preservation for 3-5 min and then implementing flash evaporation, lowering the temperature of a product after flash evaporation to 97-99° C., and subsequently carrying out heat preservation for 2-3 hours at the temperature of 95-97° C. to obtain a starch liquefaction product; while performing spray liquefaction, supplementing starch, water and medium-temperature alpha-amylase, high-temperature resistant alpha-amylase, lipase and neutral protease into the third starch milk; and (4) a saccharification step: adjusting a pH of the starch liquefaction product to 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

Favorable Effects (1) According to the present disclosure, the medium-temperature amylase, the high-temperature amylase, the lipase and the protease are used in combination in the pre-liquefaction step to carry out pre-liquefaction treatment on the high-concentration starch milk, so that the viscosity of the starch in the heating and gelatinization process at the liquefaction stage is effectively reduced. Furthermore, in a preferred embodiment, the viscosity of the starch during the heat gelatinization process in the liquefaction stage is more effectively reduced by performing a two-step pre-liquefaction treatment and a continuous liquefaction of the starch milk. The method can treat the high-concentration starch milk under the action of spray liquefaction, thereby performing the continuous liquefaction of the high-concentration starch and further carrying out the continuous production of the starch saccharification product.

(2) According to the method in the present disclosure, the dry basis mass fraction of the starch liquefied product may reach 40 wt %-70 wt %; the DE value is within a range of 22-28. Furthermore, in the continuous liquefaction embodiment, the dry basis mass fraction of the starch liquefaction product may be within a range of 50-70 wt %. The flocculation phenomenon of protein in the starch liquefaction product obtained by the liquefaction step is obvious, and the protein precipitates float on the surface of the starch liquefaction product, such that the starch liquefaction product obtained after liquefaction has high filtration velocity, the starch liquefaction product is clear and has less impurities, it is beneficial for implementing the subsequent separation process and saccharification process. In contrast to the filtration velocity of 4 mL/min of the normal production standard, the filtration velocity of the starch liquefaction product may reach 4.5 mL/min-19 mL/min.

(3) The present disclosure uses an efficient composite saccharifying enzyme containing pullulanase and glucoamylase and being free of transglucosidase as an enzyme preparation in the saccharifying step to catalyze the saccharifying reaction, such that the composite reaction is effectively inhibited, and the yield of starch saccharification products is improved; the DX value of the starch saccharification product is more than 95% (DX must be more than 95% as required by the industrial production standards).

(4) The method in the present disclosure increases the initial starch milk concentration in the production process of the starch saccharification product (starch sugar) from 33 wt % in the prior art to a range of 38 wt %-55 wt %, breaks through the production process of two stages of high-concentration liquefaction and saccharification, and the indexes of the starch liquefaction product and the starch saccharification product are completely in compliance with the production standards, thereby reducing the steam consumption in the evaporation process before the subsequent glucose isomerization section. In addition, the problems such as high pressure and difficult filtration often occur in the plate-and-frame filtration of the high-concentration saccharification liquid, and the process can solve the problem of difficult filtration during the saccharification process and ensure the continuous operation of production. Therefore, the method of the present disclosure can ensure the yield of glucose in the starch saccharification product in the saccharification stage, and further produce the effects of decreasing energy consumption, improving productivity, reducing cost and improving efficiency.

BRIEF DESCRIPTION OF THE DRAWINGS

The accompanying drawings are provided here to facilitate further understanding on the present disclosure, and constitute a part of this document. They are used in conjunction with the following embodiments to explain the present disclosure, but shall not be comprehended as constituting any limitation to the present disclosure.

FIG. 1 schematically shows the results of measuring viscosity of the first starch milks of the Example 1, Comparative Example 4, Comparative Example 5 and Comparative Example 6.

DETAILED DESCRIPTION

In order to facilitate comprehensive understanding of the present disclosure, the invention is further described below with reference to the embodiments, but the embodiments should not be construed as any limitation thereto.

In an embodiment, the present disclosure provides a method for producing starch saccharification products by using high-concentration starch milk, which comprises the following steps:

(1) a pre-liquefaction step: adding medium-temperature alpha-amylase, high-temperature resistant alpha-amylase, lipase and neutral protease into starch milk having a pH of 5.0-6.0 and a dry basis mass fraction of 38 wt %-55 wt %, mixing and preserving heat at a temperature of 45-60° C., preferably 55-60° C. for 0.5~1.5 hours to obtain a first starch milk;

(2) a liquefaction step: performing spray liquefaction on the first starch milk, carrying out heat preservation for 3-5 min and then implementing flash evaporation, lowering the temperature of a product after flash evaporation to 97-99° C., and subsequently carrying out heat preservation for 0.5-3 hours at a temperature of 95-97° C. to obtain a starch liquefaction product; and (3) a saccharification step: adjusting a pH of the starch liquefaction product to a range of 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

Unless otherwise specified, the "starch milk" in the present disclosure refers to a starch emulsion prepared by blending starch and water; the "high-concentration starch milk" refers to starch milk-like substance having a dry basis mass fraction of starch within a range of 38-55 wt %.

The step (1) is a pre-liquefaction step, and the starch milk having a dry basis mass fraction of 38-55 wt % is pre-liquefied in the pre-liquefaction step to obtain a pre-liquefied product (i.e., a first starch milk).

In a preferred embodiment, the starch milk in the step (1) is prepared in a size mixing tank at a temperature of 45-60° C. by taking corn starch as a raw material; preferably, the starch milk has a dry basis mass fraction of 40-45 wt %.

In a preferred embodiment, in the step (1), the starch milk is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of the starch. An use of the enzyme mixture may effectively reduce viscosity of the starch milk while pre-liquefying the starch milk. The medium temperature alpha-amylase used in the present disclosure may be medium temperature alpha-amylase 480-B produced by the Novozymes Biotechnology Co., Ltd., the high-temperature resistant alpha-amylase may be high-temperature resistant alpha-amylase POWERLIQ produced by the Genenco (China) Biological Engineering Co., Ltd., the lipase may be the lipase produced by the Shandong Longkete Enzyme Preparation Co., Ltd., and the neutral protease may be the medium temperature protease PWN10160 produced by the Novozymes Biotechnology Co., Ltd. For the sake of balancing the optimal activity conditions for the enzymes, the pre-liquefaction step is performed at a pH of 5.0-6.0 and a temperature of 45-60° C.

In the step (1), the first starch milk has a Brix value of 9-18%, preferably 13-17%. The Brix value described herein has the meaning well-known in the art, the value reflects the concentration of soluble solids in a liquid.

In a preferred embodiment, in the step (2), the first starch milk is discharged from the size mixing tank into a spray gun, and the first starch milk is sprayed out through a spray gun port and subsequently contacted with high-pressure steam to perform the spray liquefaction. In the present disclosure, the spray liquefaction process refers to that the starch milk meets high-pressure steam at the spray gun port, and the starch milk is heated instantly and subjected to shearing force to be uniformly dispersed and hydrolyzed by enzyme due to the small size of the spray gun port, thereby performing the spray liquefaction.

In a further preferred embodiment, the first starch milk in the step (2) is discharged from the size mixing tank at a speed of 0.1-0.2 m³/h. Preferably, the temperature of the spray gun port is 100-110° C., and the pressure of the high-pressure steam is within a range of 0.5 MPa-0.7 MPa.

In the present disclosure, the "high-pressure steam" refers to water vapor having a saturated vapor pressure of 0.5 MPa-0.7 MPa, such as 0.6 MPa.

In a preferred embodiment, the heat preservation in step (2) is performed in a maintaining tube for 3-5 min. The material after the spray liquefaction needs to flow through a section of maintaining tube for heat preservation, such that the high-temperature enzymes (medium-temperature alpha-amylase and high-temperature resistant alpha-amylase) continuously play a role, and the spray liquefaction effect is more desirable. The time of heat preservation can be altered by adjusting the length of the maintaining tube as required, and preferably, the heat preservation is performed in the maintaining tube for 3 min.

In a preferred embodiment, the flash evaporation in step (2) is carried out in a flash evaporation tank.

In the step (2), the DE value of the starch liquefaction product is within a range of 22-28 and a dry basis mass fraction of 40 wt %-70 wt %.

In the step (3), a pH conditioning agent is used for adjusting a pH of the starch liquefaction product. The present disclosure does not impose a particular limitation on the pH conditioning agent, as long as the pH conditioning agent can fulfill the purpose of the present disclosure. Just as an example, the pH conditioning agent is 8M hydrochloric acid.

Unless otherwise specified, the term "composite saccharifying enzyme" in the present disclosure refers to an enzyme that is formulated with pullulanase and glucoamylase and removes transglucosidase, the composite saccharifying enzyme is capable of further saccharifying a starch liquefaction product into a starch saccharification product containing glucose and inhibiting the occurrence of composite reaction. In a preferred embodiment, 0.2 wt‰-0.7 wt‰, preferably 0.4 wt‰-0.7 wt‰, of composite saccharifying enzyme is added in the step (3) relative to the weight of the starch liquefaction product. The ratio of pullulanase to glucoamylase in the composite saccharifying enzyme is not particularly limited as long as it can fulfill the purpose of the present disclosure. Preferably, the composite saccharifying enzyme is an ultra1.0 composite saccharifying enzyme containing pullulanase and glucoamylase and having glucosyltransferase removed, which is produced by the Bestzyme Biotech Limited.

In another embodiment, the present disclosure relates to a method for continuously producing starch saccharification products by using high-concentration starch milk, which comprises the following steps:

(1) a first pre-liquefaction step: adding medium-temperature alpha-amylase, high-temperature resistant alpha-amylase, lipase and neutral protease into starch milk having a pH of 5.0-6.0 and a dry basis mass fraction of 38 wt %-55 wt %, and preserving heat at a temperature of 45-60° C., preferably at 55-60° C. for 0.5-1.5 hours to obtain a first starch milk;

(2) a second pre-liquefaction step: adding starch into the first starch milk and stirring to obtain a second starch milk having a dry basis mass fraction of 50 wt %-70 wt %, adding medium-temperature alpha-amylase, high-temperature resistant alpha-amylase, lipase and neutral protease into the second starch milk, and preserving heat at a temperature of 50-60° C. for more than 0.5 hour to obtain a third starch milk;

(3) a liquefaction step: performing spray liquefaction on the third starch milk, carrying out heat preservation for 3-5 min and then implementing flash evaporation, lowering the temperature of a product after flash evaporation to 97-99° C., and subsequently carrying out heat preservation for 2-3 hours at the temperature of 95-97° C. to obtain a starch liquefaction product; while performing spray liquefaction, supplementing starch, water and medium-temperature alpha-amylase, high-temperature resistant alpha-amylase, lipase and neutral protease into the third starch milk; and (4) a saccharification step: adjusting a pH of the starch liquefaction product to 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

The step (1) is a first pre-liquefaction step, the starch milk with a dry basis mass fraction of 38-55 wt % is subjected to first pre-liquefaction to obtain a first pre-liquefaction product (i.e., a first starch milk).

In a preferred embodiment, the starch milk in the step (1) is prepared in a size mixing tank at a temperature of 45-60° C. by taking corn starch as a raw material; preferably, the starch milk has a dry basis mass fraction of 40-45 wt %.

In a preferred embodiment, in step (1), the starch milk is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch. For the sake of balancing the optimal activity conditions for the enzymes, the pre-liquefaction step is performed at a pH of 5.0-6.0 and a temperature of 45-60° C.

In the step (1), the first starch milk has a Brix value of 9-18%, preferably 13-17%.

In the step (2), a second pre-liquefaction is performed by adding starch and medium temperature alpha-amylase, high-temperature resistant alpha-amylase, lipase and neutral protease to the first starch milk (first pre-liquefaction product).

In a preferred embodiment, the first starch milk in step (2) is stirred and added with starch having a dry mass fraction greater than 70 wt %, preferably greater than 80 wt % (e.g. 87 wt %).

In a preferred embodiment, the second starch milk in step (2) is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch.

In the step (2), the third starch milk has a Brix value of 10-24%, preferably 22-24%.

In a preferred embodiment, the third starch milk in the step (3) is discharged from the size mixing tank into a spray gun, and the third starch milk is sprayed out through a spray gun port and subsequently contacted with high-pressure steam to perform the spray liquefaction. In a further preferred embodiment, in the step (3), the third starch milk is discharged from the size mixing tank at a speed of 0.1-0.2 m³/h. Preferably, the temperature of the spray gun port is within a range of 100-110° C., and the pressure of the high-pressure steam is within a range of 0.5 MPa-0.7 MPa, preferably 0.6 MPa-0.7 MPa. In a preferred embodiment, the heat preservation in the step (3) is performed in a maintaining tube, and the flash evaporation is performed in a flash evaporation tank.

While the spray liquefaction is performed in the step (3), the size mixing tank is continuously replenished with water, starch, medium temperature alpha-amylase, high-temperature resistant alpha-amylase, lipase and neutral protease. Through the supplement of the materials, the continuous liquefaction of the starch milk can be realized.

In a preferred embodiment, the starch is supplemented in step (3) at a rate of 110-120 kg/h. Preferably, the water is replenished at a rate of 80-90 kg/h.

In a preferred embodiment, in the step (3), the medium temperature alpha-amylase, the high-temperature resistant alpha-amylase, the lipase and the neutral protease are supplemented in the following ratio: 0.1 wt‰-0.4 wt‰ of medium-temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch.

In a preferred embodiment, in step (3), the starch and water are supplemented such that the obtained material has a dry basis mass fraction within a range of 50 wt %-70 wt %. Although the obtained material has a dry basis content of 50 wt %-70 wt %, the viscosity of the third starch milk is not too high due to the two-step pre-liquefaction process, and the pressure required for spray liquefaction is only 0.5 MPa-0.7 MPa. A liquefaction ejector (e.g., a spray gun) is used for spraying steam to the starch milk film, the liquefaction ejector enables the starch milk to be quickly heated to complete gelatinization and liquefaction in a short time, so that the insoluble starch particles are dispersed at a high temperature, the number of the insoluble starch particles is greatly reduced, the obtained starch liquefied product is transparent and easy to filter, and the sugar yield of the starch is high. In addition, the flash evaporation process is adopted to further concentrate the liquefied liquid.

In the step (3), the starch liquefaction product has a DE value within a range of 22-28 and a dry basis mass fraction within a range of 50 wt %-70 wt %.

In a preferred embodiment, 0.2 wt‰-0.7 wt‰, preferably 0.4 wt‰-0.7 wt‰, of the composite saccharifying enzyme is added in the step (4) relative to the weight of the starch liquefaction product. In the step (4), the starch saccharification product has a DX value more than 95% and a Brix value within a range of 40-70%. In the present disclosure, the DX-value has the meaning well-known in the art, which is a percentage of the glucose content in the sugar solution relative to the dry substance, i.e. the glucose yield. In the present disclosure, the well-known methods in the art are used as the measurement method of the DX value. In the present disclosure, medium temperature amylase is an amylase whose enzyme activity at 60-85° C. can still reach more than 60% of the enzyme activity under optimal conditions. High temperature amylase is an amylase whose enzyme activity at 90-110° C. can still reach more than 60% of the enzyme activity under optimal conditions.

EXAMPLES

The present disclosure will be described below with reference to specific examples, but the present disclosure is not limited thereto. The steam injection device used in the example is commercially available from Shanghai Xiaole East-tide Biotechnology development Co., Ltd with a model number ESCS-M104. The high-quality corn starch used in the examples is purchased from COFCO Biochemical Energy (Gongzhuling) Co., Ltd. with a dry basis mass fraction of 87 wt %. The medium temperature alpha-amylase is commercially available from Novozymes (China) Biotechnology Co., Ltd. with a product number 480-B; the high-temperature resistant alpha-amylase is purchased from Genenco (China) Biological Engineering Co., Ltd. under the trade name POWERLIQ; the lipase is commercially available from Shandong Longket enzyme preparation Co., Ltd with a product name lipase, the neutral protease is purchased from Novozymes (China) Biotechnology Co., Ltd. with a product number PWN 10160; the composite saccharifying enzyme is commercially available from Bestzyme Biotech Limited (the product number is Bestzyme ultra 1.0); the saccharifying enzyme is purchased from the Genenco (China) Biological Engineering Co., Ltd. (the product number is Optimax4060 VHP). Unless otherwise specified, the experimental methods used in the following examples are conventional methods; the reagents, materials and the like used in the following examples are commercially available unless otherwise specified.

In the Examples of the present disclosure, the measurement method of the DE value of the sample solution is as follows:

1. Solution preparation (a) Methine blue indicator solution (10 g/L): weighing 1.0 g of methylene blue, adding water to dissolve the methylene blue and fixing the volume to 100 mL.

(b) Glucose standard solution (2 g/L): weighing 0.5000 g (precisely weighing to 0.0001 g) of standard anhydrous glucose dried to a constant weight at a temperature of 100±2° C., adding water to dissolve glucose and fixing the volume to 250 mL.

(c) Preparation of Fehling solution

Fehling solution I: weighing 69.3 g of copper sulfate ($CuSO_4.5H_2O$), adding water to dissolve the copper sulfate and fixing the volume to 1,000 mL, and storing the copper sulfate in a brown bottle;

Fehling solution II: Weighting up 346.0 g of potassium sodium tartrate ($KNaC_4H_4O_6.4H_2O$) and 100.0 g of sodium hydroxide, dissolving the compounds in water to form an aqueous solution and fixing the volume to 1,000 mL, then storing the solution in a rubber-sealed glass bottle. Sucking up supernatant liquid for use if the precipitate exists before use;

2. Calibration: when the pre-titration is performed, 5.0 mL of the Fehling solution II and 5.0 mL of the Fehling solution I are sequentially sucked into a conical flask, 20 mL of water is added, 3 glass beads are added, 24 mL of glucose standard solution is further added, the solution in the conical flask is shaken up to a homogeneous solution, and the conical flask is heated, the solution is controlled to boil within a time range of 120±15 s and is kept at a slightly boiling state, 2 droplets of methylene blue indicator solution are added, the titration is continued by using the glucose standard solution until the end point that the blue color just disappears, the whole titration operation shall be accomplished within 3 min. When the formal titration is performed, the glucose standard solution with a volume which is less than the glucose standard solution consumed by the titration by 1 mL is added in advance, a parallel test is carried out, the total volume of the consumed glucose standard is recorded, and the arithmetic mean value of the total volume is calculated.

The mass of glucose consumed by 5 mL of the Fehling solution II and 5 mL of the Fehling solution I is calculated according to formula (1):

$$RP = \frac{m_1 \times V_1}{250} \quad (1)$$

in the formula:

RP: the mass of glucose consumed by 5 mL of the Fehling solution II and 5 mL of the Fehling solution I, the unit is gram (g);

$m_1$: weighing the amount of standard anhydrous glucose, the unit is g;

$V_1$: the total volume of the consumed glucose standard solution, the unit is mL.

3. Measurement of DE value in sample solution (a) Preparation of sample solution Weighing a certain amount of sample solution, the sample amount is taken on condition of meeting the requirement of titration, it is appropriate to arrange that sample solution per 100 mL contains 125-200 mg (precisely weighing to 0.0001 g) of reducing sugar, adding hot water to dissolve the reducing sugar, and fixing the volume of sample solution to 250 mL by using water.

(b) Pre-titration

Sequentially sucking 5.0 mL of the Fehling solution II and 5.0 mL of the Fehling solution I into a conical flask, adding 20 mL of water, adding 3 glass beads, adding part of the sample solution in advance, heating the conical flask, controlling the solution to boil within a time range of 120±15 s, keeping a slightly boiling state, dropwise adding the sample solution at the speed of 1 droplet per 2 seconds until the blue color of the solution will disappear, adding 2 droplets of the methine blue indicator solution, continuously dropwise adding the sample solution until the end point that the blue color just disappears, and recording the total volume of the consumed sample solution.

(c) Formal titration

Sucking 5.0 mL of the Fehling solution II and 5.0 mL of the Fehling solution I sequentially into a conical flask, adding a pre-titrated sample solution into the conical flask with a volume which is less than the pre-titration sample solution by 1 mL, heating the conical flask, controlling the solution to boil within a time range of 120±15 s and keeping a slightly boiling state, dropwise adding the sample solution at the speed of 1 droplet per 2 seconds, adding 2 droplets of a methine blue indicator solution when the blue color of the solution is about to disappear, continuously dropwise adding the sample solution until the end point that the blue color just disappears, accomplishing the whole titration operation within 3 min, recording the total volume of the consumed sample solution, and calculating the DE value in the sample solution according to a formula (2):

$$DE = \frac{RP}{m_2 \times \frac{V_2}{250} \times DMC} \times 100\% \quad (2)$$

in the formula:

DE value: the equivalent value of glucose in the sample solution, %;

RP: the mass of glucose consumed by 5 mL of the Fehling solution II and 5 mL of the Fehling solution I, the unit is gram (g);

$m_2$: the sampling amount, g;

$V_2$: the total volume of the consumed sample solution in the titration process, mL;

DMC: the content of syrup dry substance (solid content) in the sample solution, %. The DMC is also called as a Brix value in the technical field.

In the embodiment of the present disclosure, the method for measuring the sample solution DMC/Brix value comprises the following steps:

1. Instrument calibration

The refractive index of Abbe refractometer (with a precision of 0.0001 unit) corrected by redistilled distilled water at 20° C. is 1.3330, which is equivalent to zero content of the dry substance (solid content) soluble saccharide substance, i.e. the Brix value is 0.

2. Measuring the DMC/Brix value (a) The refractometer prism is opened, a small amount of sample solution (1-2 droplets) is dripped into the center of the prism surface by a glass rod, and the prism is closed quickly. The prism surface is uniformly distributed with the sample solution, there is no bubble and the visual field is filled with the sample solution.

(b) Keeping the constant temperature to be 20.0±0.1° C., and using an ocular lens for reading the refractive index (accurately reading the index to 0.0001) and the percentage content of the dry substance (solid) soluble carbohydrate, namely the Brix value of the sample solution.

Examples 1-4: Production of Starch Saccharification Products by Using High-Concentration Starch Milk Example 1

(1) a pre-liquefaction step: taking commercially available corn starch as a raw material, preparing starch milk having a dry basis mass fraction of 45 wt % in a size mixing tank at a temperature of 50° C., adjusting a pH to 6.0 by using 8M hydrochloric acid, adding 0.15 wt‰ of medium-temperature alpha-amylase, 0.2 wt‰ of high-temperature resistant alpha-amylase, 0.04 wt‰ of lipase and 0.07 wt‰ of neutral protease into the starch milk in the size mixing tank based on the dry basis starch of the starch milk, mixing together, and then preserving heat at a temperature of 55° C. for 0.5 hour to obtain a first starch milk with a Brix value of 15%.

(2) a liquefaction step: discharging the first starch milk from a size mixing tank into a spray gun through a pipeline at the speed of 0.18 m³/h, spraying the first starch milk through a spray gun port, and contacting with high-pressure steam (the pressure is 0.6 MPa) to carry out spray liquefaction, wherein the temperature of the spray gun port is 108° C.; keeping the temperature of the material after the injection liquefaction in a maintaining pipe for 3 minutes, and then the material entering a flash evaporation tank to perform flash evaporation; lowering temperature of the material after the flash evaporation to 98° C., and subsequently preserving heat at a temperature of 95° C. for 2 hours to obtain a starch liquefaction product.

As indicated by the measurement results, the obtained starch liquefied product has a DE value of 25 and a dry basis mass fraction of 44.3 wt %. The protein flocculates and floats on the starch liquefaction product. The starch liquefaction product is filtrated by using a No. 101 filter paper having a diameter of 150 mm, the filtration rate is to filter out 47 mL of clarified saccharification liquid every 4 min (i.e., about 12 mL/min).

(3) a saccharification step: adjusting a pH of the starch liquefaction product to a range of 4.0-4.5 with 8M hydrochloric acid, lowering the temperature to 60° C., adding 0.4 wt‰ of composite saccharifying enzyme (Bestzyme ultra1.0), and performing heat preservation at 60° C. for 40 hours to carry out saccharifying process, so as to prepare starch saccharification product with glucose yield (a DX value) of 95.2% and a Brix value of 45.2%.

Example 2

(1) a pre-liquefaction step: taking commercially available corn starch as a raw material, preparing starch milk having a dry basis mass fraction of 40 wt % in a size mixing tank at a temperature of 50° C., adjusting a pH to 6.0 by using 8M hydrochloric acid, adding 0.2 wt‰ of medium-temperature alpha-amylase, 0.2 wt‰ of high-temperature resistant alpha-amylase, 0.08 wt‰ of lipase and 0.12 wt‰ of neutral protease into the starch milk in the size mixing tank based on the dry basis starch of the starch milk, mixing together, and then preserving heat at a temperature of 55° C. for 0.5 hour to obtain a first starch milk with a Brix value of 13%.

(2) a liquefaction step: discharging the first starch milk from a size mixing tank into a spray gun through a pipeline at the speed of 0.18 m³/h, spraying the first starch milk through a spray gun port, and contacting with high-pressure steam (the pressure is 0.6 MPa) to carry out spray liquefaction, wherein the temperature of the spray gun port is 108° C.; keeping the temperature of the material after the injection liquefaction in a maintaining pipe for 3 minutes, and then entering a flash evaporation tank for performing flash evaporation; lowering the temperature of a material after the flash evaporation to 98° C., and subsequently preserving heat at a temperature of 95° C. for 2 hours to obtain a starch liquefaction product.

As indicated by the measurement results, the obtained starch liquefied product has a DE value of 22.5 and a dry basis mass fraction of 40.2 wt %. The protein flocculates and floats on the starch liquefaction product. The starch liquefaction product is filtrated by using a No. 101 filter paper having a diameter of 150 mm, the filtration rate is to filter out 75 mL of clarified saccharification liquid every 4 min (i.e., about 19 mL/min).

(3) a saccharification step: adjusting a pH of the starch liquefaction product to a range of 4.0-4.5 with 8M hydrochloric acid, lowering the temperature to 60° C., adding 0.4 wt‰ of composite saccharifying enzyme (Bestzyme ultra1.0), and performing heat preservation at 60° C. for 36 hours to carry out saccharifying process, so as to prepare a starch saccharification product with glucose yield (a DX value) of 95.6% and a Brix value of 40.2%.

Example 3

A starch saccharification product is produced by using the same pre-liquefaction step (1) and liquefaction step (2) as those steps in Example 1, except for an use of the following saccharification step (3):

A saccharification step (3): adjusting a pH of the starch liquefaction product obtained from the liquefaction step (2) in Example 1 to a range of 4.0-4.5 with hydrochloric acid, lowering the temperature to 60° C., adding 0.5 wt‰ of composite saccharifying enzyme (Bestzyme ultra1.0), and performing heat preservation at 60° C. for 40 hours to carry out saccharifying process, so as to prepare a starch saccharification product with glucose yield (DX value) of 95.6% and a Brix value of 45.3%.

Example 4

A starch saccharification product is produced by using the same pre-liquefaction step (1) and liquefaction step (2) as those steps in Example 1, except for an use of the following saccharification step (3):

A saccharification step (3): adjusting a pH of the starch liquefaction product obtained from the liquefaction step (2) in Example 1 to a range of 4.0-4.5 with hydrochloric acid, lowering the temperature to 60° C., adding 0.7 wt‰ of composite saccharifying enzyme (Bestzyme ultra1.0), and performing heat preservation at 60° C. for 40 hours to carry out saccharifying process, so as to prepare a starch saccharification product with glucose yield (a DX value) of 96.2% and a Brix value of 44.9%.

Examples 5-6: Continuous Production of Starch Saccharification Products by Using High-Concentration Starch Milk

Example 5

(1) A first pre-liquefaction step: taking commercially available corn starch as a raw material, preparing starch milk having a dry basis mass fraction of 45 wt % in a size mixing tank at a temperature of 50° C., adjusting a pH to 6.0 by using 8M hydrochloric acid, adding 0.25 wt‰ of medium-temperature alpha-amylase, 0.2 wt‰ of high-temperature resistant alpha-amylase, 0.06 wt‰ of lipase and 0.1 wt‰ of neutral protease into the starch milk in the size mixing tank based on the dry basis starch of the starch milk, mixing together, and then preserving heat at a temperature of 55° C. for 1 hour to obtain a first starch milk with a Brix value of 15%.

(2) A second pre-liquefaction step: adding corn starch into the first starch milk and stirring to obtain a second starch milk having a dry basis mass fraction of 55 wt %, adding 0.25 wt‰ of medium-temperature alpha-amylase, 0.2 wt‰ of high-temperature resistant alpha-amylase, 0.06 wt‰ of lipase and 0.1 wt‰ of neutral protease into the size mixing tank based on the dry basis starch of the starch milk, mixing together, and then preserving heat at a temperature of 55° C. for 0.5 hour to obtain a third starch milk with a Brix value of 24%.

(3) A liquefaction step: discharging the third starch milk from a size mixing tank into a spray gun through a pipeline at the speed of 0.18 m³/h, spraying the third starch milk through a spray gun port, and contacting with high-pressure steam (the pressure is 0.6 MPa) to carry out spray liquefaction, wherein the temperature of the spray gun port is 108° C.; keeping the temperature of the material after the injection liquefaction in a maintaining pipe for 3 minutes, and then the material entering a flash evaporation tank to perform flash evaporation; lowering temperature of the material after the flash evaporation to 98° C., and subsequently preserving heat at a temperature of 95° C. for 2 hours to obtain a starch liquefaction product; replenishing water into the size mixing tank at a speed of 85 kg/h while performing spray liquefaction; replenishing corn starch into the size mixing tank at the speed of 114.8 kg/h, and simultaneously supplementing 0.25 wt‰ of medium-temperature alpha-amylase, 0.2 wt‰ of high-temperature resistant alpha-amylase, 0.06 wt‰ of lipase and 0.1 wt‰ of neutral protease (based on the dry basis starch), thereby performing the continuous spray liquefaction.

As indicated by the measurement results, the obtained starch liquefied product has a DE value of 26.3 and a dry basis mass fraction of 51.2 wt %. The protein flocculates and floats on the starch liquefaction product. The starch liquefaction product is filtrated by using a No. 101 filter paper having a diameter of 150 mm, the filtration rate is to filter out 39 mL of clarified saccharification liquid every 4 min (i.e., about 10 mL/min).

(4) A saccharification step: adjusting a pH of the starch liquefaction product to a range of 4.0-4.5 with 8M hydrochloric acid, lowering the temperature to 60° C., adding 0.6 wt‰ of composite saccharifying enzyme (Bestzyme ultra1.0), and performing heat preservation at 60° C. for 40 hours to carry out saccharifying process, so as to prepare starch saccharification product with a DX value of 95.1% and a Brix value of 51.6%.

Example 6

(1) A first pre-liquefaction step: taking commercially available corn starch as a raw material, preparing starch milk having a dry basis mass fraction of 45 wt % in a size mixing tank at a temperature of 50° C., adjusting a pH to 6.0 by using 8M hydrochloric acid, adding 0.35 wt‰ of medium-temperature alpha-amylase, 0.25 wt‰ of high-temperature resistant alpha-amylase, 0.08 wt‰ of lipase and 0.12 wt‰ of neutral protease into the starch milk in the size mixing tank based on the dry basis starch of the starch milk, mixing together, and then preserving heat at a temperature of 55° C. for 1.5 hour to obtain a first starch milk with a Brix value of 17%.

(2) A second pre-liquefaction step: adding corn starch into the first starch milk and stirring to obtain a second starch milk having a dry basis mass fraction of 70 wt %, adding 0.35 wt‰ of medium-temperature alpha-amylase, 0.25 wt‰ of high-temperature resistant alpha-amylase, 0.08 wt‰ of lipase and 0.12 wt‰ of neutral protease into the size mixing tank based on the dry basis starch of the starch milk, mixing together, and then preserving heat at a temperature of 55° C. for 0.5 hour to obtain a third starch milk with a Brix value of 22%.

(3) A liquefaction step: discharging the third starch milk from a size mixing tank into a spray gun through a pipeline at the speed of 0.18 m³/h, spraying the third starch milk through a spray gun port, and contacting with high-pressure steam (the pressure is 0.6 MPa) to carry out spray liquefaction, wherein the temperature of the spray gun port is 108° C.; keeping the temperature of the material after the injection liquefaction in a maintaining pipe for 3 minutes, and then the material entering a flash evaporation tank to perform flash evaporation; lowering temperature of the material after the flash evaporation to 98° C., and subsequently preserving heat at a temperature of 95° C. for 2 hours to obtain a starch liquefaction product; replenishing water into the size mixing tank at a speed of 85 kg/h while performing spray liquefaction; replenishing corn starch into the size mixing tank at the speed of 114.8 kg/h such that the material in the size mixing tank has a dry basis mass fraction of 70 wt %, and simultaneously supplementing 0.35 wt‰ of medium-temperature alpha-amylase, 0.25 wt‰ of high-temperature resistant alpha-amylase, 0.08 wt‰ of lipase and 0.12 wt‰ of neutral protease (based on the dry basis starch), thereby performing the continuous spray liquefaction.

As indicated by the measurement results, the obtained starch liquefied product has a DE value of 25.7 and a dry basis mass fraction of 66.3 wt %; the protein flocculates and floats on the starch liquefaction product. The starch liquefaction product is filtrated by using a No. 101 filter paper having a diameter of 150 mm, the filtration rate is to filter out 18 mL of clarified saccharification liquid every 4 min (i.e., about 4.5 mL/min).

(4) A saccharification step: adjusting a pH of the starch liquefaction product to a range of 4.0-4.5 with 8M hydrochloric acid, lowering the temperature to 60° C., adding 0.7 wt‰ of composite saccharifying enzyme (Bestzyme ultra1.0), and performing heat preservation at 60° C. for 40 hours to carry out saccharifying process, so as to prepare starch saccharification product with a DX value of 95.0% and a Brix value of 66.8%.

Comparative Examples 1-3: Effect of Using Different Composite Saccharifying Enzymes in the Saccharification Step (3) on the Yield of Starch Saccharification Product Relative to Example 1

Comparative Example 1

A starch saccharification product is produced by using the same pre-liquefaction step (1) and liquefaction step (2) as those steps in Example 1, except for an use of the following saccharification step (3):

A saccharification step (3): adjusting a pH of the starch liquefaction product obtained from the liquefaction step (2) in Example 1 to a range of 4.0-4.5 with hydrochloric acid, lowering the temperature to 60° C., adding 0.4 wt‰ of a saccharifying enzyme with a product number Optimax4060 VHP produced by the Genenco (China) Biological Engineering Co., Ltd., and performing heat preservation at 60° C. for 40 hours to carry out saccharifying process, so as to prepare a starch saccharification product with a DX value of 91.2% and a Brix value of 45.3%.

Comparative Example 2

A starch saccharification product is produced by using the same pre-liquefaction step (1) and liquefaction step (2) as those steps in Example 1, except for an use of the following saccharification step (3):

A saccharification step (3): adjusting a pH of the starch liquefaction product obtained from the liquefaction step (2) in Example 1 to a range of 4.0-4.5 with hydrochloric acid, lowering the temperature to 60° C., adding 0.5 wt‰ of a saccharifying enzyme with a product number Optimax4060 VHP produced by the Genenco (China) Biological Engineering Co., Ltd., and performing heat preservation at 60° C. for 40 hours to carry out saccharifying process, so as to prepare a starch saccharification product with a DX value of 91.8% and a Brix value of 44.8%.

Comparative Example 3

A starch saccharification product is produced by using the same pre-liquefaction step (1) and liquefaction step (2) as those steps in Example 1, except for an use of the following saccharification step (3):

A saccharification step (3): adjusting a pH of the starch liquefaction product obtained from the liquefaction step (2) in Example 1 to a range of 4.0-4.5 with hydrochloric acid, lowering the temperature to 60° C., adding 0.7 wt‰ of a saccharifying enzyme with a product number Optimax4060 VHP produced by the Genenco (China) Biological Engineering Co., Ltd., and performing heat preservation at 60° C. for 40 hours to carry out saccharifying process, so as to prepare a starch saccharification product with a DX value of 93.6% and a Brix value of 45.2%.

As can be seen, that the glucose yields obtained in Comparative Examples 1, 2 and 3 are lower than the glucose yield (a DX value) of 95% or more obtained in the saccharification step (3) of Example 1, which uses the composite saccharifying enzyme containing pullulanase and glucoamylase and removing transglucosidase.

Comparative Examples 4-6: effect of using different combinations of enzymes in the pre-liquefaction step (1) on the filtration rate of the starch liquefaction product relative to Example 1

Comparative Example 4

A pre-liquefaction step (1): taking commercially available corn starch as a raw material, preparing starch milk having a dry basis mass fraction of 45 wt % in a size mixing tank at a temperature of 50° C., adjusting the pH to 6.0 by using 8M hydrochloric acid, adding 0.15 wt‰ of medium-temperature alpha-amylase and 0.2 wt‰ of high-temperature resistant alpha-amylase into the starch milk in the size mixing tank based on the dry basis starch of the starch milk, mixing together, and then preserving heat at a temperature of 55° C. for 1 hour to obtain a first starch milk with a Brix value of 13%.

The starch liquefaction product is produced by using the same liquefaction step (2) as that in Example 1.

As indicated by the measurement results, the obtained starch liquefied product has a DE value of 20.7. The starch liquefaction product is filtrated by using a No. 101 filter paper having a diameter of 150 mm, the filtration rate is to filter out 20 mL of clarified saccharification liquid every 4 min.

Comparative Example 5

The steps performed in Comparative Example 5 are substantially identical with those in Comparative Example 4, the difference merely resides in that 0.15 wt‰ of medium temperature alpha-amylase, 0.2 wt‰ of high-temperature resistant alpha-amylase and 0.04 wt‰ of lipase are added in the pre-liquefaction step (1).

As indicated by the measurement results, the obtained starch liquefied product has a DE value of 23.7. The starch liquefaction product is filtrated by using a No. 101 filter paper having a diameter of 150 mm, the filtration rate is to filter out 28 mL of clarified saccharification liquid every 4 min.

Comparative Example 6

The steps performed in Comparative Example 6 are substantially identical with those in Comparative Example 4, the difference merely resides in that 0.15 wt‰ of medium temperature alpha-amylase, 0.2 wt‰ of high-temperature resistant alpha-amylase and 0.07 wt‰ of neutral protease are added in the pre-liquefaction step (1).

As indicated by the measurement results, the obtained starch liquefied product has a DE value of 22.4. The starch liquefaction product is filtrated by using a No. 101 filter paper having a diameter of 150 mm, the filtration rate is to filter out 42 mL of clarified saccharification liquid every 4 min.

It is demonstrated that as compared with the high filtration rates (4.5 mL/min-19 mL/min) obtained by using the medium temperature amylase, the high temperature amylase, the lipase and the protease in combination in the pre-liquefying step (1) of Example 1, the filtration rates of the starch liquefaction products obtained in Comparative Example 4, Comparative Example 5 and Comparative Example 6, which do not use the above-described combination of enzyme of the present disclosure, are decreased correspondingly.

Test Example: Measurement of the Viscosity of the First Starch Milks in Example 1 and Comparative Examples 4, 5 and 6

30 g of the first starch milk to be measured are poured into a sample tank of an RVA viscometer, the program is set as follows: performing heat preservation at a temperature of 60° C. for 1.5 min, then raising the temperature to 95° C. with a required time of 6 min., keeping the temperature at 95° C. for 5.5 min., then cooling to 50° C. with a required time of 2.5 min, setting the rotating speed to be 250 rpm, and measuring the viscosity in the liquefaction process. The results of viscosity measurement on the first starch milks of Example 1, Comparative Example 4, Comparative Example 5 and Comparative Example 6 are as shown in FIG. 1, wherein the a-curve is the blank control group, the b-curve shows viscosity curve of the sample taken in Comparative Example 4, the c-curve illustrates viscosity curve of the sample taken in Comparative Example 5, the d-curve shows the viscosity curve of the sample taken in Comparative Example 6, and the e-curve illustrates viscosity curve of the sample taken in Example 1.

The results show that after the sample is pretreated by four enzymes and liquefied for 5 min, the viscosity of the starch milk reaches a maximum value; when the curve a is compared with the curve e, the peak viscosity is reduced by 68.4% from 14,080 cP of the curve a to 4,440 cP of the curve e; after performing liquefaction within a time range of 7.5 min to 13 min, the viscosity of the curve e is far lower than that of the curve a, the duration of high viscosity is shortened, the effects concerning viscosity reduction amplitude of the starch milk at high temperature is very obvious, and the continuous liquefaction condition is reached due to the viscosity reduction effect.

The invention claimed is:

1. A method for producing starch saccharification products by using high-concentration starch milk, comprising the following steps:
   (1) a pre-liquefaction step: adding medium-temperature alpha-amylase, high temperature resistant alpha-amylase, lipase and neutral protease into starch milk having a pH of 5.0-6.0 and a dry basis mass fraction of 38 wt %-55 wt %, mixing and preserving heat at a temperature of 45-60° C. for 0.5-1.5 hours to obtain a first starch milk;
   (2) a liquefaction step: performing spray liquefaction on the first starch milk, carrying out heat preservation for 3-5 min and then implementing flash evaporation, lowering the temperature of a product after flash evaporation to 97-99° C., and subsequently carrying out heat preservation for 0.5-3 hours at a temperature of 95-97° C. to obtain a starch liquefaction product; and
   (3) a saccharification step: adjusting a pH of the starch liquefaction product to a range of 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

2. The method according to claim 1, wherein the starch milk in the step (1) is prepared in a size mixing tank at a temperature of 45-60° C. by taking corn starch as a raw material.

3. The method according to claim 1, wherein the starch milk is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of the starch.

4. The method according to claim 1, wherein the first starch milk in the step (2) is discharged from the size mixing tank into a spray gun, and the first starch milk is sprayed out through a spray gun port and subsequently contacted with high-pressure steam to perform the spray liquefaction.

5. The method according to claim 4, wherein the first starch milk is discharged from the size mixing tank at a speed of 0.1-0.2 m³/h.

6. The method according to claim 4, wherein the temperature of the spray gun port is 100-110° C., and the pressure of the high-pressure steam is within a range of 0.5 MPa-0.7 MPa.

7. The method according to claim 1, wherein 0.2 wt‰-0.7 wt‰ of composite saccharifying enzyme is added in step (3) relative to the weight of the starch liquefaction product.

8. The method according to claim 7, wherein 0.4 wt‰-0.7 wt‰, of composite saccharifying enzyme is added in step (3) relative to the weight of the starch liquefaction product.

9. A method for continuously producing starch saccharification products by using high-concentration starch milk, comprising the following steps:
   (1) a first pre-liquefaction step: adding medium-temperature alpha-amylase, high-temperature resistant alpha-amylase, lipase and neutral protease into starch milk having a pH of 5.0-6.0 and a dry basis mass fraction of 38 wt %-55 wt %, and preserving heat at a temperature of 45-60° C. for 0.5-1.5 hours to obtain a first starch milk;
   (2) a second pre-liquefaction step: adding starch into the first starch milk and stirring to obtain a second starch milk having a dry basis mass fraction of 50 wt %-70 wt %, adding medium-temperature alpha-amylase, high-temperature resistant alpha-amylase, lipase and neutral protease into the second starch milk, and preserving heat at a temperature of 50-60° C. for more than 0.5 hour to obtain a third starch milk;
   (3) a liquefaction step: performing spray liquefaction on the third starch milk, carrying out heat preservation for 3-5 min and then implementing flash evaporation, lowering the temperature of a product after flash evaporation to 97-99° C., and subsequently carrying out heat preservation for 2-3 hours at the temperature of 95-97° C. to obtain a starch liquefaction product; while performing spray liquefaction, supplementing starch, water and medium-temperature alpha-amylase, high-temperature resistant alpha-amylase, lipase and neutral protease into the third starch milk; and
   (4) a saccharification step: adjusting a pH of the starch liquefaction product to 4.0-4.5, lowering the temperature to 60-62° C., adding a composite saccharifying enzyme containing pullulanase and glucoamylase and removing transglucosidase, and carrying out heat preservation and saccharification for 36-40 hours at the temperature of 60-65° C. to produce starch saccharification products.

10. The method according to claim 9, wherein the starch milk in the step (1) is prepared in a size mixing tank at a temperature of 45-60° C. by taking corn starch as a raw material.

11. The method according to claim 9, wherein the starch milk is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch.

12. The method according to claim 9, wherein the second starch milk in step (2) is added with 0.1 wt‰-0.4 wt‰ of medium temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch.

13. The method according to claim 9, wherein the third starch milk in the step (3) is discharged from the size mixing tank into a spray gun, and the third starch milk is sprayed out through a spray gun port and subsequently contacted with high-pressure steam to perform the spray liquefaction.

14. The method according to claim 13, wherein the third starch milk is discharged from the size mixing tank at a speed of 0.1-0.2 m³/h.

15. The method according to claim 13, wherein the temperature of the spray gun port is within a range of 100-110° C., and the pressure of the high-pressure steam is within a range of 0.5 MPa-0.7 MPa.

16. The method according to claim 9, wherein the heat preservation is performed in a maintaining tube, and the flash evaporation is performed in a flash evaporation tank.

17. The method according to claim 9, wherein in the step (3), the starch is supplemented at a rate of 110-120 kg/h, and the water is replenished at a rate of 80-90 kg/h, the starch and water are supplemented such that the obtained material has a dry basis mass fraction within a range of 50-70 wt %.

18. The method according to claim 9, wherein the medium temperature alpha-amylase, the high-temperature resistant alpha-amylase, the lipase and the neutral protease are supplemented in the following ratio: 0.1 wt‰-0.4 wt‰ of medium-temperature alpha-amylase, 0.2 wt‰-0.3 wt‰ of high-temperature resistant alpha-amylase, 0.04 wt‰-0.08 wt‰ of lipase and 0.07 wt‰-0.12 wt‰ of neutral protease on a dry basis of starch.

19. The method according to claim 8, wherein 0.2 wt‰-0.7 wt‰ of the composite saccharifying enzyme is added in the step (4) relative to the weight of the starch liquefaction product.

20. The method according to claim 19, wherein 0.4 wt‰-0.7 wt‰ of the composite saccharifying enzyme is added in the step (4) relative to the weight of the starch liquefaction product.

* * * * *